United States Patent [19]

Zenitz

[11] 4,021,431

[45] May 3, 1977

[54] 3-(PIPERIDINO-LOWER-ALKYL)-INDOLES

[75] Inventor: Bernard L. Zenitz, Colonie, N.Y.

[73] Assignee: Sterling Drug Inc., New York, N.Y.

[22] Filed: Nov. 20, 1975

[21] Appl. No.: 633,939

Related U.S. Application Data

[60] Division of Ser. No. 439,279, Feb. 4, 1974, which is a continuation-in-part of Ser. No. 261,739, June 12, 1972, abandoned.

[52] U.S. Cl. .................. 260/293.61; 260/326.15; 424/267; 424/274
[51] Int. Cl.² ........................................ C07D 401/06
[58] Field of Search ............... 260/293.61, 326.15

[56] References Cited

UNITED STATES PATENTS

| | | | |
|---|---|---|---|
| 3,238,215 | 3/1966 | Zenitz | 260/293 |
| 3,285,908 | 11/1966 | Shen | 260/211 |
| 3,527,761 | 9/1970 | Archibald et al. | 260/293 |
| 3,564,009 | 2/1971 | Yamamoto et al. | 260/326.16 |
| 3,686,213 | 8/1972 | Poletto et al. | 260/326.15 |

FOREIGN PATENTS OR APPLICATIONS 5,205M  7/1967  France

*Primary Examiner*—G. Thomas Todd
*Attorney, Agent, or Firm*—William G. Webb; B. Woodrow Wyatt

[57] ABSTRACT

1-Acyl-3-(amino-lower-alkyl)indoles, useful as anti-inflammatory agents, are prepared either by acylation of a 3-(amino-lower-alkyl)indole; by Fisher indole synthesis from an N'-acylphenylhydrazine and an amino-lower-alkanone; by alkylation of an amine with a 1-acyl-3-(halo-lower-alkyl)indole; or by reductive alkylation of a 1-acyl-3-indole-lower-alkylcarboxaldehyde.

2 Claims, No Drawings

3-(PIPERIDINO-LOWER-ALKYL)-INDOLES

This is a division of my prior, copending application Ser. No. 439,279, filed Feb. 4, 1974, which in turn is a continuation-in-part of my earlier application Ser. No. 261,739, filed June 12, 1972, copending with application Ser. No. 439,279, and now abandoned.

This invention relates to 1-acyl-3-(amino-lower-alkyl)-indoles which are useful as anti-inflammatory agents and which have the formula:

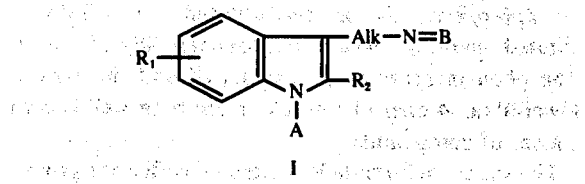

I where Alk is lower-alkylene; $R_1$ is hydrogen or from one to two members of the group consisting of lower-alkyl, lower-alkoxy, lower-alkylmercapto, halogen (including fluorine, chlorine or bromine), trifluoromethyl, trifluoromethoxy, hydroxy, benzyloxy, amino, lower-alkylamino and di-lower-alkylamino; $R_2$ is hydrogen, lower-alkyl, hydroxymethyl or carbo-lower-alkoxy; A is lower-alkanoyl, cycloalkylcarbonyl, cycloalkyl-lower-alkanoyl, 2-hydrindenoyl, benzoyl, cinnamoyl, 2-thenoyl, 2-furoyl, 2-, 3- or 4-pyridinecarbonyl, or benzenesulfonyl; and N=B is a member selected from the group consisting of

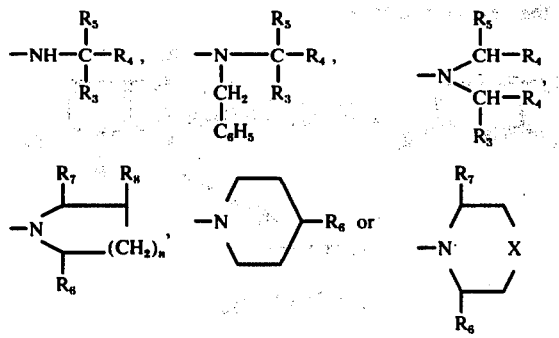

where $R_3$ and $R_4$ are each lower-alkyl; $R_5$ is hydrogen or lower-alkyl; $R_6$ is lower-alkyl, cycloalkyl or cycloalkyl-lower-alkyl; $R_7$ and $R_8$ each are hydrogen, lower-alkyl, cycloalkyl or cyclo-alkyl-lower-alkyl; X is O, S or N-$R_3$; and n is one of the integers 1, 2 and 3, and wherein the phenyl ring of A when benzoyl, cinnamoyl or benzenesulfonyl can be substituted by from one to two members of the group consisting of lower-alkyl, lower-alkoxy, lower-alkylmercapto, lower-alkylsulfinyl, lower-alkylsulfonyl, halogen (including fluorine, chlorine or bromine), hydroxy or a single methylenedioxy, to acid-addition salts thereof, and to methods for their preparation.

As used herein, the terms "lower-alkyl" and "lower-alkoxy" mean saturated, monovalent aliphatic radicals, including straight or branched-chain radicals, having from one to four carbon atoms in the lower-alkyl moiety, as illustrated by, but not limited to, methyl, ethyl, propyl, isopropyl, butyl, and the like.

As used herein, term "lower-alkanoyl" means saturated radicals derivved from a mono-carboxylic acid, which can be straight or branched, and containing from one to four carbon atoms, as illustrated by, but not limited to formyl, acetyl, propionyl, butyryl, and isobutyryl.

As used herein, the terms "cycloalkyl" or "cycloalkyl-lower-alkyl" mean saturated, carbocyclic radicals having from three to seven ring carbon atoms and from one to five carbon atoms in the lower-alkyl moiety, as illustrated by, but not limited to cyclopropyl, cyclopropylmethyl, cyclobutyl, cyclopentyl, cyclohexyl, cyclohexylmethyl, 2-cyclohexylethyl, cycloheptyl, and the like.

As used herein, the term "lower-alkylene" means a divalent, saturated radical, which can be straight or branched, and having from two to seven carbon atoms, as illustrated by, but not limited to 1,2-ethylene [-$CH_2CH_2$-], 1,3-propylene [$CH_2CH_2CH_2$-], 1,2-(1-methylethylene) [-$CH(CH_3)CH_2$-], 1,2-(2-methylethylene) [-$CH_2CH(CH_3)$-], 1,4-butylene [-$CH_2CH_2CH_2CH_2$-], 1,5-pentylene [-$CH_2CH_2CH_2CH_2CH_2$-], 1,5-(1,1-dimethylpentylene) [-$C(CH_3)_2CH_2CH_2CH_2CH_2$], and the like.

One method for the preparation of the compounds of formula I comprises reaction of an appropriate acyl halide with the anion of an appropriate 3-(amino-lower-alkyl)indole of formula II, which is prepared by reacting the 3-(amino-lower-alkyl)-indole with a strond base, for example, an alkali metal hydroxide, an alkali metal hydride, an alkali metal amide, or an alkali metal lower-alkoide, in an organic solvent inert under the conditions of the reaction, for exmple, toluene, xylene, or N,N-dimethylformamide, the latter hereinafter referred to as DMF. The reaction takes place at temperatures from around 10° C. to about 50° C. It is preferred to carry out the reaction at room temperature in DMF and in the presence of an excess over theoretical equivalent of both the strong base and the acyl halide, a preferred strong base being an alkali metal hydride, for example sodium hydride. The method is represented by the following reaction:

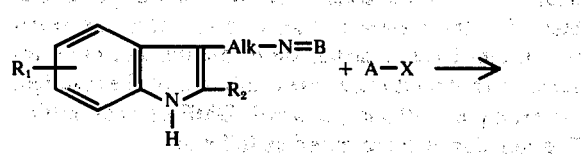

II

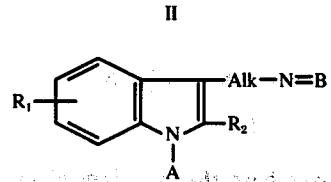

I where $R_1$, $R_2$, A, Alk and N=B have the meanings given above, and X represents halogen.

The starting material represented by formula II are generally known compounds, many of which are generally described in U.S. Pat. Nos. 3,238,215 and 3,578,669. As disclosed therein, the 3-(amino-lower-alkyl)indoles represented by formula II are advantageously prepared by Fischer indole synthesis involving reaction of an appropriate phenylhydrazine of formula III with an appropriate amino-lower-alkanone of formula IV or a ketal thereof. The method is illustrated by the following reaction sequence where $R_1$, $R_2$, Alk and N=B have the meanings given above:

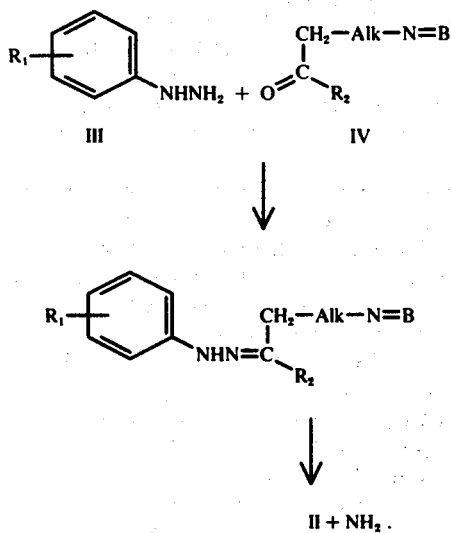

As indicated, the reaction takes place in two steps involving the formation first of a hydrazone, which then rearranges and cyclizes under the conditions of the reaction with loss of a molecule of ammonia to form the compounds of formula II. The reaction is carried out at a temperature in the range from about 20° C. to about 150° C. in an organic solvent inert under the conditions of the reaction, for example, ethanol, methanol, isopropanol, glacial acetic acid, and the like, and in the presence of an acid catalyst, for example, sulfuric acid, hydrochloric acid, glacial acetic acid, zinc chloride, cuprous chloride, or boron trifluoride.

The compounds of formula IV are prepared by reaction of an appropriate amine, H—N=B of formula VI, with a 1-halo-lower-alkan-4-one of formula V or a ketal thereof in the presence of an acid-acceptor, for example an alkali metal carbonate or biarbonate, in an organic solvent inert under the conditions of the reaction, for example methanol, ethanol, DMF or acetonitrile. The reaction is represented as follows:

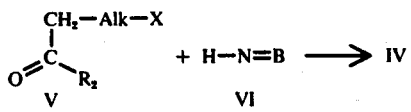

where $R_2$, Alk, X and N=B have the meanings given above.

The amines of formula VI where —N=B is the group:

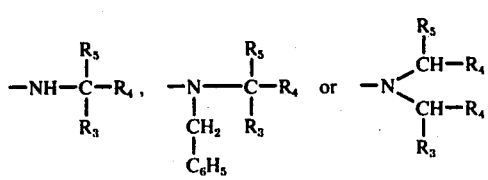

are known compounds.

Those where —N=B is the group:

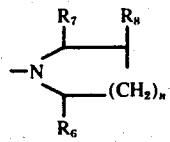

where n is 2 are old, having been generally described in U.S. Pat. No. 3,238,215. As described therein, they are prepared by catlytic reduction over platinum oxide of an appropriate 2- or 3-substituted (or 2,6-disubstituted)-pyridine, which are commercially available. The phenylhydrazines of formula III and the 1-halo-lower-alkan-4-ones of formula V are both well-known classes of compounds.

The amines of formula VI where —N=B is the group:

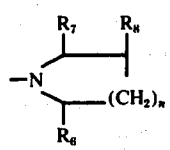

where n is the integer 1 are prepared by refluxing a mixture of an appropriate alkanedione, ammonium acetate and glacial acetic acid, and catalytic reduction over platinum oxide of the resulting pyrrole according to the reaction scheme:

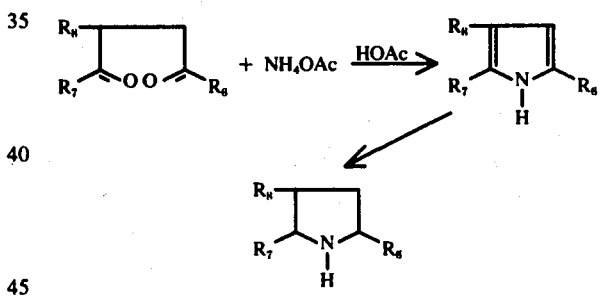

where $R_6$, $R_7$ and $R_8$ have the meanings given above.

Alternatively, the amines of formula VI where — N = B is the group:

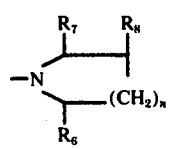

where $n$ is 1 $R_8$ is H are prepared by reaction of a Grignard reagent, $R_6MgX$, with a 4-$R_7$-4-halobutyronitrile,

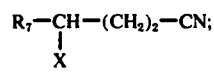

direct cyclization of the resulting 1-amino-1-$R_6$-4-$R_7$-4-halo-butene; and catalytic reduction of the resulting 2-$R_6$-5-$R_7$-4,5-dihydropyrrole as indicated by the reaction sequence:

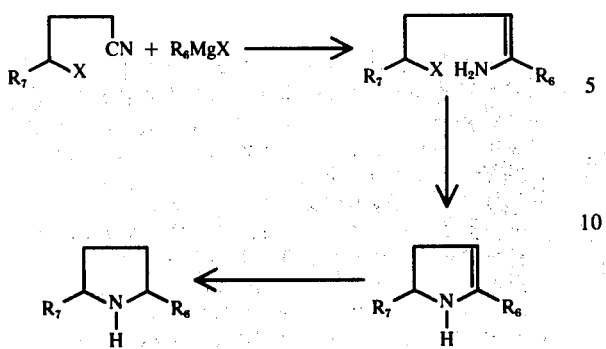

The amines of formula VI where —N=B is the group:

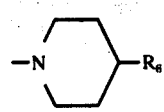

are advantageously prepared, like the amines where —N=B is the group:

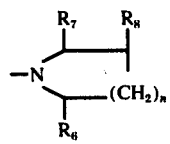

where n is 2, by catalytic reduction over platinum oxide of the corresponding 4-$R_6$-pyridine.

The amines of formula VI where —N=B is the group:

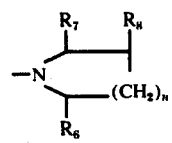

where $R_7$ and $R_8$ are hydrogen, n is the integer 3 $R_6$ has the meanings given above are prepared by Beckmann rearrangement of an appropriate $R_6$-substituted-cyclohexanone oxime and reduction, with lithium aluminum hydride, of the resulting lactam according to the reaction:

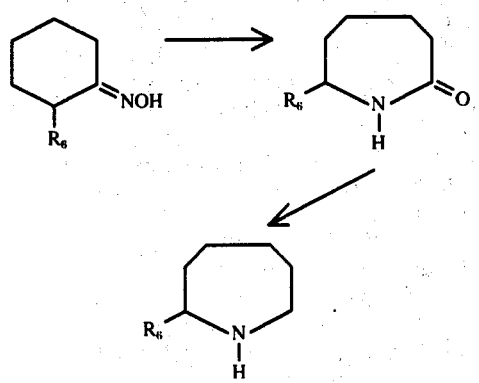

The amines of formula VI where —N=B is the group:

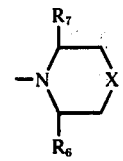

where X is O are prepared according to the method described in British Pat. No. 835,717 which comprises passing a vaporized mixture of a glycol ether having the formula

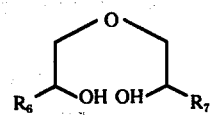

together with ammonia and hydrogen over a hydrogenation/dehydrogenation catalyst based on either nickel or cobalt at a temperture from 150° to 250° C. A preferred catalyst is nickel on kieselguhr.

The amines of formula VI where —N=B is the group:

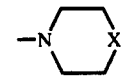

where X is S are preferably prepared by the methods described by Idson et al., J. Am. Chem. Soc. 76, 2902 (1954) which involves either the reaction of sodium sulfide with an appropriate bis-2-haloethylamine:

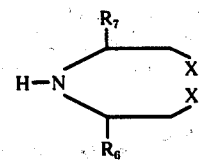

or the reaction of ammonia with an appropriate bis 2-halo-ethylsulfide:

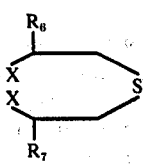

where $R_6$ and $R_7$ have the meanings given above, and X represents halogen.

Alternatively, the intermediate 3-(amino-lower-alkyl)indoles of formula II are prepared by reaction of a 3-(X'-lower-alkyl)indole of formula VII with an appropriate amine of formula VI in an enert organic solvent, for example acetone or a lower-alkanol, in the presence of an acid-acceptor, for example an alkali metal carbonate or bicarbonate, as represented by the equation:

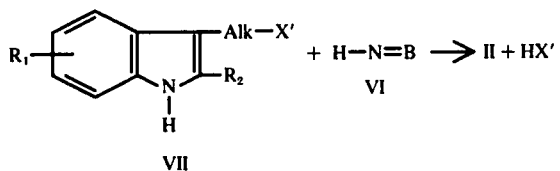

where $R_1$, $R_2$, Alk and N=B have the meanings given above, and X' is halogen, or the anion off a strong organic sulfonic acid including lower-alkylsulfonates, benzenesulfonate or toluene-sulfonate. The compounds of formula VII are a known class and are prepared by the methods described in U.S. Pat. Nos. 3,562,278 and 3,639,414.

Another method for preparing the 3-(amino-lower-alkyl)indoles of formula II where Alk is 1,2-ethylene comprises reduction, with lithium aluminum hydride, of a 3-indoleglyoxamide of formula VIII:

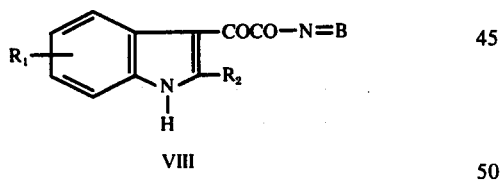

where $R_1$, $R_2$ and N=B have the meanings given above. The reaction is carried out at a temperature from 20° C. to around 100° C. in an inert organic solvent such as diethyl ether, tetrahydrofuran or dioxane. The glyoxamides of formula VIII are a known class and are prepared by the procedure described in U.S. Pat. No. 3,238,215.

Still another method for preparing the intermediate 3-(amino-lower-alkyl)indoles of formula II comprises reduction, with lithium aluminum hydride, of a 3-indole-lower-alkanamide of formula IX:

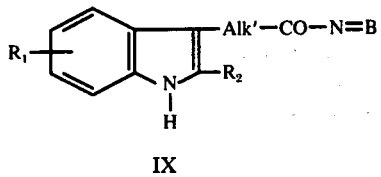

where $R_1$, $R_2$ and N=B have the meanings given above and Alk' represents divalent, saturated lower-alkylene containing from one to six carbon atoms. The reduction is carried out using the same conditions described above for the reduction of the glyoxamides of formula VIII. The amides of formula IX are a known class of compounds and are prepared by the procedures described in U.S. Pat. No. 3,238,215.

The compounds of formula I can also be prepared by reaction of an appropriate amino-lower-alkanone of formula IV above with an N'-acylphenylhydrazine of formula X:

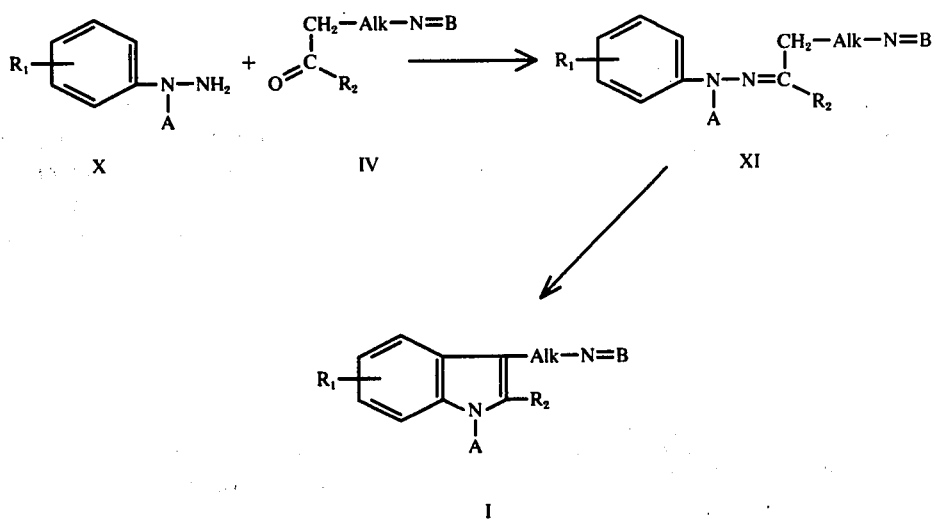

where $R_1$, $R_2$, A, Alk and N=B have the meanings given above. The reaction is preferably carried out in an organic solvent, for example glacial acetic acid, methanol, ethanol, isopropanol or benzene, and in the presence of an acidic catalyst, for example mineral acids, organic carboxylic and sulfonic acids, polyphosphonic acid, boron trifluoride, and the like. As indicated, the hydrazone of formula XI is first formed during the course of the reaction, and this intermediate can, if desired, be isolated, but no particular advantage is gained thereby, and it is preferred to allow the reaction to go all the way to completion with the formation of the final products of formula I.

The N'-acylphenylhydrazines of formula X are prepared by reaction of an appropriate N-acylaniline with an alkali metal hydride, for example sodium hydride, in DMF, and reaction of the resulting alkali metal salt with chloramine (prepared by reaction of concentrated ammonium hydroxide with aqueous hypochlorous acid). The method is represented by the reactions:

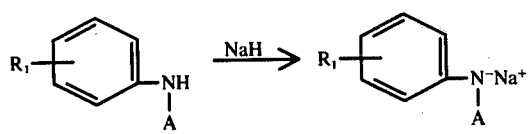

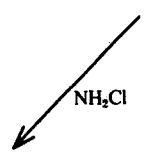

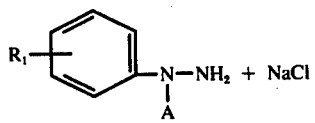

where $R_1$ and A have the meanings given above.

Another method for preparing the final products of formula I comprises reaction of a 1-acyl-3-($X'$-lower-alkyl)indole of formula XII with an appropriate amine of formula VI, preferably in an inert organic solvent, for example lower-alkanols or acetone, and preferably in the presence of an acid acceptor, for example alkali metal carbonates or bicarbonates or a molar excess of the amine, H—N=B. The method is represented by the reaction:

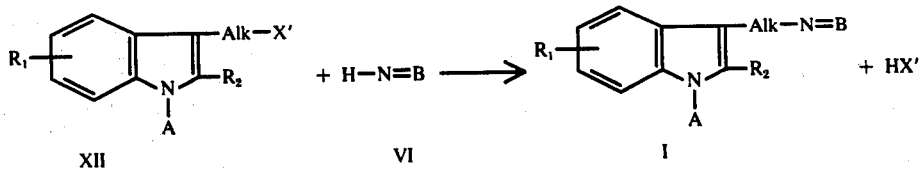

where $R_1$, $R_2$, A, Alk, N=B and $X'$ have the meanings given above.

The 1-acyl-3-($X'$-lower-alkyl)indoles of formula XII in turn are prepared by acylation, using the procedure described above, of the corresponding 3-($X'$-lower-alkyl)indoles which are a known class of compounds.

A still further method for the preparation of the compounds of formula I where N=B is one of the groups

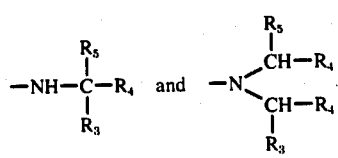

where $R_3$, $R_4$ and $R_5$ have the meanings given above comprises alkylation, with either one or two moles of an appropriate lower-alkyl ester

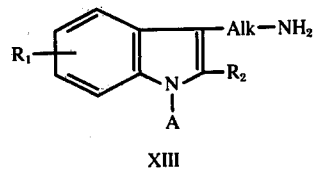

of the corresponding primary amine of formula XIII:

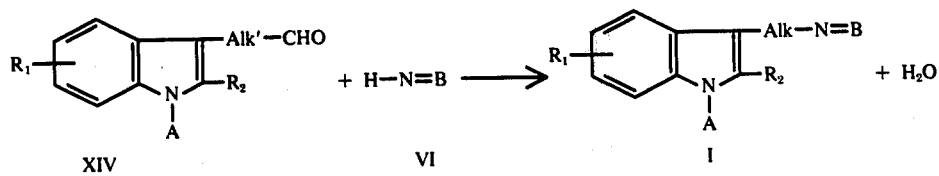

where $R_1$, $R_2$, $R_3$, $R_4$, $R_5$, A, Alk and $X'$ have the meanings given above. The reaction is preferably carried out in an inert organic solvent, for example DMF, lower-alkanols or acetone, and preferably in the presence of an acid-acceptor, for example an alkali metal carbonate or bicarbonate or an excess of the amine starting material.

The amines of formula XIII are in turn prepared by any of the methods described above for preparing the final products of formula I where N=B has the meanings given above.

Another method for preparing the final products of formula I comprises the reductive alkylation with hydrogen over a catalyst of an appropriate amine of formula VI with an appropriate 1-acyl-3-indole-lower-alkylcarboxaldehyde of formula XIV according to the reaction:

where $R_1$, $R_2$, A, Alk' and N=B have the meanings given above. The reaction is carried out at hydrogen pressures in the range from 2–150 atmospheres at a temperature in the range from 40°–150° C. and in an organic solvent inert under the conditions of the reaction, for example lower-alkanols, petroleum ether, glacial acetic acid, and the like. Suitable catalysts are platinum, nickel and palladium. Platinum and Raney nickel are preferred catalysts.

The aldehydes of formula XIV are a generally known class and are prepared by the method described in U.S. Pat. Nos. 3,576,800 and 3,627,783 which comprises reacting an N'-acylphenylhydrazine of formula X with an appropriate ketoaldehyde acetal of formula XV in a Fisher indole synthesis and acid hydrolysis of the terminal acetal group according to the reaction:

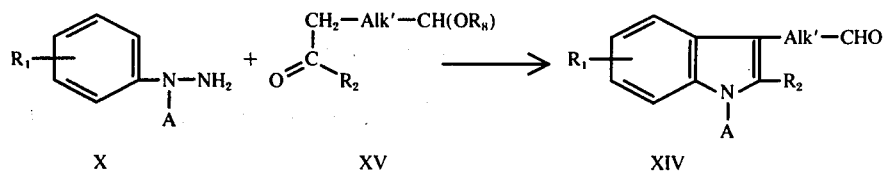

where $R_1$, $R_2$, A and Alk' have the meanings given above, and $R_8$ is lower-alkyl.

The novel compounds of the instant invention are the compounds of formula I and the acid-addition salts thereof. The compounds of formula I in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to all of the compounds of formula I, whether in the form of the free base or in the form of the acid-addition salts of the base. I have found that by virtue of this common structural entity, the bases and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases is not vitiated by side effects ascribable to the anions.

In utilizing this pharmacological activity of the salts of the invention, I prefer, of course, to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example, by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of my new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new 1-acyl-3-(amino-lower-alkyl)indoles and not in any particular acid moiety or acid anion associated with the salt forms of my compounds; rather, the acid moieties or anions which can be associated in the salt forms are in themselves neither novel nor critical and therefore can be any acid anion or acid-like substance capable of salt formation with the bases. In fact, in aqueous solutions, the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic aicd, isethionic acid, benzenesulfonic acid, p-toluene-sulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

In standard pharmacological test procedures, the compounds of formula I have been found to possess anti-inflammatory activity and are useful as anti-inflammatory agents. Anti-inflammatory activity was determined using (1) the inhibition of carrageenin-induced foot edema test essentially described by Van Arman et al., J. Pharmacol. Exptl. Therap. 150, 328 (1965) as modified by Winter et al., Proc. Soc. Exp. Biol. and Med. 111, 544 (1962) and (2) a modification of the inhibition of adjuvant-induced arthritis test described by Pierson, J. Chronic Diseases 16, 863 (1963) and Glenn et al., Am. J. Vet. Res. 26, 1180 (1965).

The inhibition of carrageenin-induced foot edema test used in the evaluation of the instant compounds is described briefly as follows: Food was withheld for approximately 18 hours prior to medication from young, male Sprague-Dawley strain rats weighing 100–110 g. used as test animals, but animals were permitted free access to drinking water up to the time of medication. The test drug was suspended by trituration in 1% gum tragacanth and administered by gavage in a volume of 1 ml./100 g. of body weight. Control animals received the gum tragacanth only. One hour after medication, 0.05 ml, of a 1% suspension of carrageenin in 0.9% saline was injected into the plantar tissue of the left hind paw. Three hours after injection of the carrageenin, edema formation, that is the increase in foot volume between the injected left hind paw as compared with the uninjected right hind paw was measured plethysmographically in the unanesthetized animal. The extended paw was immersed to the top of the most proximal callus pad into a mercury filled glass cylinder connected to a Statham pressure transducer and the impulse amplified and recorded by a polygraph. The polygraph was standardized for each assay so that a 3.6 mm. deflection on the recording paper was equivalent to 0.1 ml. volume. The results were expressed as percent inhibition calculated from the average differences in foot volume between the control and medicated rats.

The inhibition of adjuvant-induced arthritis test used in the evaluation of the instant compounds if described briefly as follows: Adult male Sprague-Dawley strain rats weighing 200–230 grams were used; 0.1 ml. of a 0.6% suspension of adjuvant (M. Butyricum, Difco Laboratories, Detroit, Michigan) in heavy mineral oil was injected into the plantar tissue of the left hind paw. A negative control group was injected with mineral oil only. Symptoms of polyarthritis began to appear approximately ten days after adjuvant administration, and beginning on the ninth day after adjuvant injection, the animals were given, by gavage, twelve daily medications of the test compounds suspended in 1% gum tragacanth in a volume of 1 ml./100 g. of body weight. Both the negative control and adjuvant injected control animals received the vehicle only. Food and water are permitted ad libitum. Twenty-four hours after the last medication, the animals were weighed, the degree of arthritic involvement (that is the increase in foot edema measured plethysmographically as described above), and plasma inflammation units were determined. The results were expressed as percent inhibition calculated from the average differences in total foot volume of both hind paws between the adjuvant injected control and medicated rats, correcting for difference in foot volume of the oil injected negative control group.

Following foot volume measurements, the animals were anesthetized with ether and bled by heart puncture into rubber stoppered, evacuated glass tubes (calibrated to draw 2.7 ml.) containing 0.3 ml. of 0.1M sodium oxalate solution for determination of plasma inflammation units (P.I.U.). The unclotted blood was centrifuged, and 0.1 ml. of the plasma was diluted with 5.0 of 0.9% sodium chloride solution. The P.I.U.'s are direct spectrophotometer optical density readings expressed as the difference between preheated and heated plasma, corrected for 1:50 dilution. The results were expressed as percent inhibition calculated from the difference between the average plasma uncorrected for average plasma inflammation units of oil-injected negative control rats.

The compounds of the invention can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

1-Benzoyl-3-[2-(2-cyclohexylmethylpiperidino)ethyl]-5-methoxy-2-methylindole

In three separate runs, 33.8 g. (0.20 mole) portions of 2-benzylpyridine, each in a solution of about 225 ml. of ethanol and 22 ml. of concentrated hydrochloric acid, were reduced over 4.0 g. portions of platinum oxide catalyst under about 54 pounds psig. of hydrogen at a temperature of about 55°–61° C. When reduction was complete in each case, the catalyst was removed by filtration, washed with small portions of ethanol, and the combined filtrates evaporated to a volume of about 80 ml. and diluted to approximately 500 ml. with boiling acetone. The solid which precipitated was collected, washed with acetone and dried giving a combined yield of 124.8 g. of 2-cyclohexylmethylpiperidine hydrochloride, m.p. 211°–213° C. The free base was regenerated from the hydrochloride by neutralization of an aqueous solution of the latter with anhydrous potassium carbonate, extraction of the oily base into benzene, evaporation of the benzene solution to dryness, and distillation of the residual oil in vacuo at 55°–59° C./0.27 mm. There was thus obtained 89.4g. of 2-cyclohexylmethylpiperidine.

A solution of 229.0 g. (0.65 mole) of anhydrous potassium carbonate, 199.3 g. (1.65 mole) of 5-chloro-2-pentanone, and 75.1 g. (0.41 mole) of 2-cyclohexylmethylpiperidine in 750 ml. of acetonitrile was heated under reflux for 72 hours, allowed to cool to room temperature, and the precipitated solid was removed by filtration and washed with small portions of acetonitrile. The combined filtrates were evaporated to dryness in vacuo, and the residual oily residue distilled in vacuo, the product, 1-(2-cyclohexylmethylpiperidino)-pentan-4-one (91.5 g., $n_D^{26}$ 1.4871), being collected at 120°–128° C./0.26-0.16 mm.

A solution of 6.0 g. (0.02 mole) of 1-(2-cyclohexylmethylpiperidino)pentan-4-one hydrochloride and 3.5 g. (0.02 mole) of 4-methoxyphenylhydrazine hydrochloride in 30 ml. of absolute ethanol was heated under reflux for five hours and then cooled in an icebath. The crystals which separated were collected, washed with cold ethanol, stirred with a mixture of ether and 10% aqueous sodium carbonate. The ether layer was separated, washed with cold water, dried, and evaporated to dryness to give 5.7 g. of light tan crystals which were recrystallized from isopropyl acetate/hexane to give 4.7 g. of 3-[2-(2-cyclohexylmethylpiperidino)ethyl]-5-methoxy-2-methylindole, m.p. 127°–129° C.

The latter (11.0 g., 0.03 mole) dissolved in 50 ml. of DMF was added dropwise with stirring over a fifteen minute period to a stirred mixture of 1.4 g. (0.03 mole) of a 57% mineral oil dispersion of sodium hydride in 50 ml. of DMF. The mixture was stirred at room temperature for two hours and then treated dropwise with stirring over a ten minute period with a solution of 4.8 g. (0.03 mole) of benzoyl chloride in 25 ml. of DMF. The yellow mixture was then stirred for an additional two hours at room temperature, diluted with 500 ml. of ether, the reaction mixture filtered, the filtrate washed with 200 ml. of water, dried, and evaporated to dryness giving 13.2 g. of a yellow viscous oil. The latter was dissolved in anhydrous ether, the solution treated with a small excess of ethanesulfonic acid, and the solid which separated after scratching with a stirring rod was collected and recrystallized from ethyl acetate giving 5.5 g of 1-benzoyl-3-[2-(2-cyclohexylmethylpiperidino)ethyl]-5-methoxy-2-methylindole ethanesulfonate, m.p. 144°–147° C.

A small amount of the ethanesulfonate salt was reconverted to the free base according to standard procedures as described above, and converted to the hydrochloride salt to give 1-benzoyl-3-[2-(2-cyclohexylmethylpiperidino)ethyl]-5-methoxy-2-methylindole hydrochloride, m.p. 225°–227° C.

EXAMPLES 2–12

Reaction of 3-[2-(2-cyclohexylmethylpiperidino)ethyl]-5-methoxy-2-methylindole, described above in Example 1, with sodium hydride and reaction of the resulting sodium salt with an appropriate acid chloride, afforded the following compounds of formula I where, in each instance, $R_1$ is 5-$CH_3O$; $R_2$ is $CH_3$; Alk is $-CH_2CH_2-$; and N=B is 2-cyclohexylmethylpiperidino. All compounds were isolated in the form of the monohydrochloride salt.

| Example | A | m.p. (° C.) | Recryst'd. from |
|---|---|---|---|
| 2 | 4-$CH_3C_6H_4CO$ | 197–199 | ethyl acetate/diethyl ether |
| 3 | 4-$CH_3OC_6H_4CO$ | 190–193 | ethyl acetate |
| 4 | 2,4-$Cl_2C_6H_4CO$ | 180–183 | ethyl acetate |
| 5 | 3,4-$Cl_2C_6H_3CO$ | 223–225 | ethyl acetate |
| 6 | 4-$FC_6H_4CO$ | 145–149 | ethyl acetate/diethyl ether |
| 7 | 2-$BrC_6H_4CO$ | 182–184 | isopropyl acetate/diethyl ether |
| 8 | $C_6H_5CH=CHCO$ | 162–168 | chloroform/hexane |
| 9 | 2-$FC_6H_4CO$ | 241–243 | methanol/diethyl ether |
| 10 | 2-thenoyl | 218–220 | ethyl acetate |
| 11 | 2-furoyl | 169–171 | ethyl acetate |
| 12 | 3-$FC_6H_4CO$ | 224–225 | acetone |

EXAMPLE 13

1-Benzoyl-3-[2-(2-cyclohexylmethylpiperidino)ethyl]-5-t-butoxy-2-methylindole is prepared by reaction of 4-t-butoxyphenylhydrazine with 1-(2-cyclohexylmethylpiperidino)pentan-4-one in ethanol and reaction of the resulting 3-[2-(2-cyclohexylmethylpiperidino)ethyl]-5-t-butoxy-2-methylindole with sodium hydride in DMF followed by reaction of the resulting sodium salt with benzoyl chloride all according to the procedure described above in Example 1.

EXAMPLE 14

1-Benzoyl-3-[2-(2-cyclohexylmethylpiperidino)ethyl]-5-methoxy-2-butylindole is prepared by reaction of 2-cyclohexylmethylpiperidine with 1-chlorooctan-4-one in ethanol in the presence of anhydrous potassium carbonate; reaction of the resulting 1-(2-cyclohexylmethylpiperidino)octan-4-one with 4-methoxyphenylhydrazine in ethanol; and reaction of the resulting 3-[2-(2-cyclohexylmethylpiperidino)ethyl]-5-methoxy-2-butylindole with sodium hydride in DMF followed by reaction of the resulting sodium salt with benzoyl chloride all according to the procedure described above in Example 1.

EXAMPLE 15

1-(2-Methylbenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 2-methylbenzoyl chloride following the procedure described above in Example 1.

EXAMPLE 16

1-(3-Methylbenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 3-methylbenzoyl chloride following the procedure described above in Example 1.

EXAMPLE 17

1-(4-t-Butylbenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 4-t-butylbenzoyl chloride following the procedure described above in Example 1.

EXAMPLE 18

1-(2-Methoxybenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 2-methoxybenzoyl chloride following the procedure described above in Example 1.

EXAMPLE 19

1-(3-Methoxybenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 3-methoxybenzoyl chloride following the procedure described above in Example 1.

EXAMPLE 20

1-(4-Isopropoxybenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in the DMF and reaction of the resulting sodium salt with 4-isopropoxybenzoyl chloride following the procedure described above in Example 1.

EXAMPLE 21

1-(2,4-Dibromobenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 2,4-dibromobenzoyl chloride following the procedure described above in Example 1.

EXAMPLE 22

1-(2,4-Difluorobenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 2,4-difluorobenzoyl chloride following the procedure described above in Example 1.

EXAMPLE 23

1-(3-Bromo-4-fluorobenzoyl)-3-[2-(2-cyclohexylmethylpiperidino)-ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 3-bromo-4-fluorobenzoyl chloride following the procedure described above in Example 1.

EXAMPLE 24

1-(2-Bromo-4-chlorobenzoyl)-3-[2-(2-cyclohexylmethylpiperidino)ethyl]-5-methoxy-2-methylindole is prepared by reaction of 3-[2-(2-cyclohexylmethylpiperidino)ethyl]-5-methoxy-2-methylindole with sodium hydride in DMF and reaction of the resulting sodium salt with 2-bromo-4-chlorobenzoyl chloride following the procedure described above in Example 1.

EXAMPLES 25–35

Reaction of 3-[2-(2-cyclohexylmethylpiperidino)ethyl]-5-methoxy-2-methylindole, described above in Example 1, with sodium hydride in DMF, and reaction of the resulting sodium salt with an appropriate acid halide, affords the following compounds of formula I where, in each instance, $R_1$ is 5-$CH_3O$; $R_2$ is $CH_3$; Alk is —$CH_2CH_2$—; and N=B is 2-cyclohexylmethylpiperidino.

| Example | A |
|---|---|
| 25 | $CH_3CO$ |
| 26 | $C_3H_7CO$ |
| 27 | cyclopropyl-CO |
| 28 | cyclohexyl-CO |
| 29 | $C_6H_5SO_2$ |
| 30 | 4-$ClC_6H_4SO_2$ |
| 31 | 4-$CH_3C_6H_4SO_2$ |

| Example | A |
|---|---|
| 32 | 4-$CH_3OC_6H_4SO_2$ |
| 33 | 4-$CH_3SC_6H_4CO$ |
| 34 | 4-$CH_3SOC_6H_4CO$ |
| 35 | 4-$CH_3SO_2C_6H_4CO$ |

EXAMPLES 36–47

Reaction of 1-(2-cyclohexylmethylpiperidino)pentan-4-one, described above in Example 1, with an appropriate phenylhydrazine afforded the following compounds of formula II where, in each instance, $R_2$ is $CH_3$; Alk is —$CH_2CH_2$—; and N=B is 2-cyclohexylmethylpiperidino. Except where noted otherwise, all compounds were isolated as the free base.

| Example | $R_1$ | m.p. (° C.) | Recryst'd. from |
|---|---|---|---|
| 36 | — | 125.4–126.6 | ethyl acetate/hexane |
| 37 | 5,6-$(CH_3O)_2$ | 100.6–1.6.2 | hexane |
| 38 | 5,7-di-F | 123–124.5 | benzene/hexane |
| 39 | 5-$CF_3O$ | 178.5–180.0 | isopropyl acetate/hexane |
| 40 | 5.7-$(CH_3)_2$ | 216–217(a) | ethanol/deithyl ether |
| 41 | 5-$C_6H_5CH_2O$ | 106–107 | isopropyl acetate/hexane |
| 42 | 5-$CH_3S$ | 1414–142 | isopropyl acetate/hexane |
| 43 | 5-$CH_3$ | 119–120.5 | isopropyl acetate/hexane |
| 44 | 5-Cl | 118–119 | isopropyl acetate/hexane |
| 45 | 5-$C_2H_5O$ | 144.5–146 | isopropyl acetate/hexane |
| 46 | 5-F | 111–112/5 | isopropyl acetate/hexane |
| 47 | 7-Cl | 201.5–202.5(b) | methanol |

(a) hydrochloride salt
(b) p-toluenesulfonate

EXAMPLES 48–59

Reaction of the compounds described above in Examples 36–47 with sodium hydride in DMF, and reaction of the resulting sodium salt with benzoyl chloride using the procedure described above in Example 1 affords the following compounds of formula I where, in each instance, $R_2$ is $CH_3$; Alk is —$CH_2CH_2$—; A is $C_6H_5CO$; and N=B is 2-cyclohexylmethylpiperidino.

| Example | $R_1$ | m.p. (° C.) | Recryst'd. from |
|---|---|---|---|
| 48 | — | 93–95(c) | |
| 49 | 5,6-$(CH_3O)_2$ | | |
| 50 | 5,7-di-F | 133–138(c) | ethyl acetate |
| 51 | 5-$CF_3O$ | | |
| 52 | 5,7-$(CH_3)_2$ | | |
| 53 | 5-$C_6H_5CH_2O$ | | |
| 54 | 5-$CH_3S$ | | |
| 55 | 5-$CH_3$ | | |
| 56 | 5-Cl | | |
| 57 | 5-$C_2H_5O$ | | |
| 58 | 5-F | 171–173(c) | isopropyl acetate |
| 59 | 7-Cl | | |

(c) hydrochloride salt

EXAMPLE 60

A mixture of 18.09 g. (0.15 mole) of 5-chloro-2-pentanone and 41.9 g. (0.42 mole) of 2-methylpiperidine in 300 ml. of acetonitrile was refluxed with stirring for twenty hours and worked up in the manner described above in Example 1. The product was converted to the hydrochloride salt to give 11.4 g. of 1-(2-methylpiperidino)pentan-4-one hydrochloride, m.p. 118°–120° C.

The latter (8.8 g., 0.04 mole) was reacted with 7.0 g. (0.04 mole) of 4-methoxyphenylhydrazine hydrochloride in 40 ml. of ethanol using the procedure described above in Example 1. There was thus obtained 8.5 g. of 3-[2-(2-methylpiperidino)ethyl]-5-methoxy-2-methylindole hydrochloride, m.p. 211°–212° C. (from ethanol).

Reaction of the latter with sodium hydride in DMF, and reaction of the resulting sodium salt with benzoyl chloride using the procedure described above in Example 1 affords 1-benzoyl-3-[2-(2-methylpiperidino)ethyl]-5-methoxy-2-methylindole.

EXAMPLE 61

Reaction of 22 g. (0.01 mole) of 1-(2-methylpiperidino)pentan-4-one, described above in Example 60, with 18 g. (0.1 mole) of 2,4-difluorophenylhydrazine hydrochloride in 100 ml. of ethanol using the procedure described in Example 1 and isolation of the product in the form of the free base gave 5.5 g. of 3-[2-(2-methylpiperidino)ethyl]-5,7-difluoro-2-methylindole, m.p. 131.5°–133.5° C. (from hexane).

Reaction of the latter with sodium hydride in DMf and reaction of the resulting sodium salt with benzoyl chloride using the procedure described above in Example 1 affords 1-benzoyl-3-[2-(2-methylpiperidino)ethyl]-5,7-difluoro-2-methylindole.

EXAMPLE 62

A mixture of 15.52 g. (0.10 mole) of 2-phenylpyridine, 15 ml. of concentrated hydrochloric acid and 2.0 g. of platinum oxide in 185 ml. of ethanol in a pressure bottle was heated and shaken in a Parr hydrogenater under 55 pounds p.s.i. of hydrogen at a temperature around 60° C. When reduction was complete in about eight hours, the catalyst was removed by filtration and the filtrate concentrated to about 50 ml. and diluted with 200 ml. of acetone. The solid which separated was collected and dried to give 14.54 g. of 2-cyclohexylpiperidine hydrochloride, m.p. 251°–253° C.

A mixture of 33.4 g. (0.2 mole) of 2-cyclohexylpiperidine, 72.4 g. (0.6 mole) of 5-chloro-2-pentanone and 82.9 g. (0.6 mole) of anhydrous potassium carbonate in 300 ml. of acetonitrile was refluxed for seventy-two hours and worked up in the manner described above in Example 1. The product was converted to the hydrochloride salt which was recrystallized from acetone to give 27.2 g. of 1-(2-cyclohexylpiperidino)pentan-4-one hydrochloride, m.p. 176°–177.5° C.

Reaction of 11.5 g. (0.04 mole) of the latter with 7.5 g. (0.04 mole) of 4-methoxyphenylhydrazine hydrochloride in 200 ml. of ethanol using the procedure described above in Example 1 and isolation of the product in the form of the hydrochloride gave 12.5 g. of 3-[2-(2-cyclohexylpiperidino)ethyl]-5-methoxy-2-methylindole hydrochloride, m.p. 270°–272° C. (from methanol/diethyl ether).

Reaction of 7.92 g. (0.02 mole) of the latter with 0.04 mole of a mineral oil dispersion of sodium hydride in 35 ml. of DMF; reaction of the resulting sodium salt with 5.62 g. (0.04 mole) of benzoyl chloride; and isolation of the product in the form of the hydrochloride salt gave 8.84 g. of 1-benzoyl-3-[2-(2-cyclohexylpiperidino)ethyl]-5-methoxy-2-methylindole hydrochloride, m.p. 232.5°–234° C. (from acetone).

EXAMPLE 63

Reaction of 4.96 g. (0.014 mole) of 3-[2-(2-cyclohexylpiperidino)ethyl]-5-methoxy-2-methylindole described above in Example 62 with 0.028 mole of a mineral oil dispersion of sodium hydride in 35 ml. of DMF; reaction of the resulting sodium salt with 4.45 g. (0.028 mole) of 4-fluorobenzoyl chloride; and isolation of the product as the hydrochloride salt gave 7.60 g. of 1-(4-fluorobenzoyl)-3-[2-(2-cyclohexylpiperidino)ethyl]-5-methoxy-2-methylindole hydrochloride, m.p. 233°–234° C. (from acetone).

EXAMPLE 64

A mixture of 9.1 g. (0.05 mole) of 2-stilbazole (Shaw et al., J. Chem. Soc. 1933, 77–79) and 1.0 g. of platinum oxide in a solution of 240 ml. of ethanol and 10 ml. of concentrated hydrochloric acid in a pressure bottle was heated and shaken on a Parr hydrogenator under about 55 pounds p.s.i.g. of hydrogen at a temperature of about 60° C. When reduction was complete in about eight hours, the catalyst was removed by filtration, the filtrate concentrated to a volume of about 50 ml. and diluted with about 200 ml. acetone. The solid which separated was collected and dried to give 9.6 g. of 2-(2-cyclohexylethyl)piperidine, m.p. 155°–156° C.

A mixtue of 19.5 g. (0.1 mole) of 2-(2-cyclohexylethyl)piperidine, 48.2 g. (0.4 mole) of 5-chloro-2-pentanone and 55.3 g. of anhydrous potassium carbonate in 200 ml. of acetonitrile was refluxed for 24 hours and worked up in the manner described above in Example 1. The product was converted to the hyrochloride to give 15.8 g. of 1-[2-(2-cyclohexylethyl)piperidino]pentan-4-one hydrochloride, m.p. 118°–119.5° C.

Reaction of 3.1 g. (0.01 mole) of the latter with 1.8 g. (0.01 mole) of 4-methoxyphenylhydrazine hydrochloride in 50 ml. of ethanol using the procedure described above in Example 1 and isolation of the product as the free base gave 2.1 g. of 3-{2-[2-(2-cyclohexylethyl)piperidino]ethyl}-5-methoxy-2-methylindole, m.p. 69°–71° C.

Reaction of 11.48 g. (0.03 mole) the latter with 0.06 mole of a mineral oil dispersion of sodium hydride in 80 ml. of DMF; reaction of the resulting sodium salt with 8.43 g. (0.06 mole) of benzoyl chloride; and isolation of the product in the form of the hydrochloride salt gave 9.4 g. of 1-benzoyl-3-{2-[2-(2-cyclohexylethyl)piperidino]ethyl}-5-methoxy-2-methylindole, m.p. 220°–221° C. (from isopropanol/ether).

EXAMPLE 65

To a solution of 24.6 g. (0.2 mole) of 4-methoxyaniline in 200 ml. of dry pyridine was added, with stirring over a 20 minute period, 31.7 g. (0.2 mole) of 4-fluorobenzoyl chloride. The mixture was stirred for one hour, diluted with 400 ml. of water, and the solid which separated was collected, washed with water and dried to give 45.8 g. of N-(4-methoxyphenyl)-4-fluorobenzamide, m.p. 188°–190° C.

A solution of 12.3 g. (0.05 mole) of the latter in 75 ml. of dry DMF was added with stirring over a 15 minute period to a stirred suspension of 1.7 g. (0.075 mole) of sodium hydride in 25 ml. of DMF, and the mixture was stirred for 1 hour. The mixture was then treated with a solution of chloramine prepared by adding 21 ml. of concentrated ammonium hydroxide to a well-stirred mixture of 130 ml. of saturated aqueous hypochlorous acid and 500 ml. of diethyl ether and separating and drying the organic layer. The resulting mixture was filtered, the filtrate taken to dryness, and the residue dissolved in ether and treated with ethereal hydrogen chloride to give 6.1 g. of N'-(4-fluorobenzoyl)-4-methoxyphenylhydrazine hydrochloride, m.p. 172°–175° C.

A mixture of the latter (4.4 g., 0.015 mole) with 4.7 g. (0.015 mole) of 1-[2-(2-cyclohexylethyl)piperidino]-pentan-4-one, described above in Example 64, in 75 ml. of ethanol was refluxed for four and a half hours and then worked up in the manner described above in Example 1. The product was isolated in the form of the hydrochloride salt to give 4.2 g. of 1-(4-fluorobenzoyl)-3-{2-[2-(2-cyclohexylethyl)-piperidino]ethyl}-5-methoxy-2-methylindole hydrochloride, m.p. 195°–197° C.

EXAMPLE 66–71

Reaction of 3-[5-(2-cyclohexylmethylpiperidino)-pentyl]-indole; 3-[2-(2-cyclohexylmethylpiperidino)ethyl]-5-methoxyindole (both disclosed in U.S. Pat. No. 3,238,215); 3-[3-(2-cyclohexylmethylpiperidino)-propyl]-7-trifluoromethylindole (m.p. 90.5°–91.5° C.); 3-[4-(2-cyclohexylmethylpiperidino)butyl]-5-chloro-7-trifluoromethylindole (m.p. 80°–81° C.) (both prepared according to the procedure described in U.S. Pat. No. 3,238,215); 3-[3-(2-cyclohexylmethyl-piperidino)propyl]-5-methoxy-2-hydroxymethylindole; or 3-[3-(2-cyclohexylmethylpiperidino)propyl]-5,7-difluoro-2-hydroxymethylindole (both disclosed in U.S. Pat. No. 3,578,669) with a mineral oil dispersion of sodium hydride in DMF, and reaction of the resulting sodium salt with benzoyl chloride using the procedure described above in Example 1, affords the respective compounds of formula I in Examples 66–71 where, in each instance, A is benzoyl and N=B is 2-cyclohexyl-methylpiperidino.

| Example | $R_1$ | $R_2$ | Alk | |
|---|---|---|---|---|
| 66 | H | H | $(CH_2)_5$ | |
| 67 | 5-$CH_3O$ | H | $CH_2CH_2$ | m.p. 192–193° C. (from acetone/ether) |
| 68 | 7-$CF_3$ | H | $(CH_2)_3$ | |
| 69 | 5-Cl-7-$CF_3$ | H | $(CH_2)_4$ | |
| 70 | 5-$CH_3O$ | $CH_2OH$ | $(CH_2)_3$ | |
| 71 | 5,7-di-F | $CH_2OH$ | $(CH_2)_3$ | |

EXAMPLE 72

A mixture of 27.6 g. (0.2 mole) of anhydrous potassium carbonate, 72.3 g. (0.6 mole) of 5-chloro-2-pentanone, 23.8 g. (0.2 mole) of potassium bromide and 32.6 g. (0.2 mole) of t-butylbenzylamine in 75 ml. of DMF was stirred at 90° C. for about 72 hours and then worked up in the manner described above in Example 1. The product was isolated in the form of the hydrochloride salt to give 8.6 g. of 1-(N-benzyl-N-t-butylamino)-pentan-4-one hydrochloride, m.p. 142°–143° C. (from acetone).

A solution of 6.6 g. (0.02 mole) of 1-(N-benzyl-N-t-butylamino)pentan-4-one hydrochloride and 4.1 g. (0.02 mole) of 4-methoxyphenylhydrazine hydrochloride in 65 ml. of absolute ethanol was heated under reflux for 2 hours and then worked up in the manner described above in Example 1. The product was isolated in the form of the hydrochloride salt which was recrystallized from ethanol to give 11.0 g. of 3-[2-(N-benzyl-N-t-butylamino)ethyl]-5-methoxy-2-methylindole, m.p. 234°–235° C.

Reaction of 21.0 g. (0.06 mole) of the latter with 0.12 mole of a mineral oil dispersion of sodium hydride in 50 ml. of DMF; reaction of the resulting sodium salt with 16.86 g. (0.12 mole) of benzoyl chloride; and isolation of the product in the form of the hydrochloride salt gave 22.8 g. of 1-benzoyl-3-[2-(N-benzyl-N-t-butylamino)ethyl]-5-methoxy-2-methylindole hydrochloride, m.p. 202°–204° C. (from acetone/ether).

A solution of 9.3 g. (0.019 mole) of the latter in 250 ml. of absolute ethanol was reduced over 1.0 g. of 10% palladium-on-charcoal under a hydrogen pressure of about 50 pounds p.s.i.g. When reduction was complete, the catalyst was removed by filtration, and the product isolated in the form of the hydrochloride salt to give 6.8 g. of 1-benzoyl-3-[2-(N-t-butylamino)ethyl]-5-methoxy-2-methylindole hydrochloride, m.p. 246°–247° C. (from ethanol/ether).

EXAMPLE 73

A mixture of 46.5 g. (0.75 mole) of ethylene glycol, 90.4 g. (0.75 mole) of 5-chloro-2-pentanone and 1.0 g. of p-toluenesulfonic acid in 400 ml. of benzene was refluxed with stirring under a water separator for about 3 hours, treated with a small amount of solid potassium carbonate, then filtered and the filtrate evaporated to dryness in vacuo. The residual oil was distilled in vacuo to give 97.5 g. of 5-chloro-2-pentanone ethylene glycol ketal, b.p. 68°–78° C./6.5–8.0 mm., $n_D^{25}$ 1.4511.

A mixture of 49.3 g. (0.3 mole) of the latter, 67.5 g. (0.66 mole) of diisopropylamine and 49.8 g. (0.3 mole) of potassium iodide in 125 ml. of DMF was heated at 90°–93° C. for about 6 hours, diluted with 1 liter of diethyl ether and the solution washed first with 10% aqueous potassium carbonate, then with water and dried. The solution was taken to dryness and the residual oil distilled in vacuo to give 41.6 g. of 2-(diisopropylamino)-4-pentanone ethylene glycol ketal, b.p. 71.5°–73° C./0.46–0.40 mm., $n_D^{27}$ 1.4480.

Reaction of 21.5 g. (0.094 mole) of the latter with 16.4 g. (0.094 mole) of 4-methoxyphenylhydrazine hydrochloride in a solution of 200 ml. of ethanol and 11.8 ml. of concentrated hydrochloric acid using the procedure described above in Example 1 and isolation of the product in the form of the free base gave 17.6 g. of 3-[2-(diisopropylamino)ethyl]-5-methoxy-2-methylindole, m.p. 58.5°–60° C.

Reaction of 11.54 g. (0.04 mole) of the latter with 0.08 mole of a mineral oil dispersion of sodium hydride in 50 ml. of DMF; reaction of the resulting sodium salt with 11.3 g. (0.08 mole) of benzoyl chloride; and isolation of the product in the form of the hydrochloride salt gave 10.4 g. of 1-benzoyl-3-[2-(diisopropylamino)ethyl]-5-methoxy-2-methylindole hydrochloride, m.p. 197°–198° C. (from isopropanol/ether).

EXAMPLES 74–77

Reaction of 4-methoxyphenylhydrazine with ethyl α-ketovalerate in ethanol using the procedure described above in Example 1; reduction with lithium aluminum hydride in tetrahydrofuran of the resulting ethyl α-(5-methoxy-2-methyl-3-indole)-acetate; reaction of the resulting 3-(2-hydroxyethyl)-5-methoxy-2-methylindole with sodium hydride in DMF, and reaction of the resulting sodium salt with benzoyl chloride using the procedure described above in Example 1; and reaction of the resulting 1-benzoyl-3-(2-hydroxyethyl)-5-methoxy-2-methylindole with thionyl bromide in benzene in the presence of calcium carbonate using the procedure described in U.S. Pat. No. 3,517,028 affords 1-benzoyl-3-(2-bromoethyl)-5-methoxy-2-methylindole. The latter, on reaction with an appropriate amine in refluxing acetone in the presence of sodium carbonate affords the compounds of formula I in Examples 72–77 below where, in each instance, $R_1$ is 5-$CH_3O$; $R_2$ is $CH_3$; A is $C_6H_5CO$; and Alk is $CH_2CH_2$.

| Example | N=B |
|---|---|
| 74 | 2,5-dimethylpyrrolidino |

-continued

| Example | N=B |
|---|---|
| 75 | 2-cyclohexylmethylhexamethyleneimino |
| 76 | 3-CH$_3$-5-C$_2$H$_5$-thiamorpholino |
| 77 | 3-butylmorpholino |

Reaction of 3-(2-chloroethyl)-5,6-dimethoxy-2-carbethoxyindole (U.S. Pat. No. 3,562,278) with 2-cyclohexylmethylpiperidine in refluxing acetone in the presence of sodium carbonate and reaction of the resulting 3-[2-(2-cyclohexylmethylpiperidino)ethyl]5,6-dimethoxy-2-carbethoxyindole with sodium hydride in DMF followed by reaction of the resulting sodium salt with benzoyl chloride affords 1-benzoyl-3-[2-(2-cyclohexylmethylpiperidino)ethyl]-5,6-dimethoxy-2-carbethoxyindole.

EXAMPLE 79

Reaction of 3-[2-(2-cyclohexylmethylpiperidino)ethyl]-5-methoxy-2-methylindole with sodium hydride in DMF, and reaction of the resulting sodium salt with 2-hydrindenoyl chloride using the procedure described above in Example 1 afords 1-(2-hydrindenoyl)-3-[2-(2-cyclohexylmethylpiperidino)ethyl]-5-methoxy-2-methylindole.

EXAMPLE 80

Reaction of 4-bromoaniline with α-cyclohexylacetyl chloride in the presence of pyridine and reaction of the resulting N-(4-bromophenyl)-α-cyclohexylacetamide with sodium hydride in DMF followed by reaction of the resulting sodium salt with chloramine all according to the procedure described in Example 65 affords N'-cyclohexylacetyl-4-bromophenylhydrazine. Reaction of the latter with levulinic aldehyde diethylacetal in refluxing ethanol using the procedure described in Example 1, and reduction of the resulting 1-cyclohexylacetyl-5-bromo-2-methylindole-3-acetaldehyde in the presence of a molar excess of 2-cyclohexylmethylpiperidine under 600 pounds p.s.i.g. of hydrogen at a temperature of 100° C. over a Raney nickel catalyst affords 1-cyclohexylacetyl-3-[2-(2-cyclohexylmethylpiperidino)ethyl]-5-bromo-2-methylindole.

EXAMPLE 81

Catalytic reduction of the 1-benzoyl-3-[2-(2-cyclohexylmethylpiperidino)ethyl]-5-benzyloxy-2-methylindole described above in Example 53 with hydrogen over a palladium-on-charcoal catalyst at about 50 pounds p.s.i.g. pressure affords 1-benzoyl-3-[2-(2-cyclohexylmethylpiperidino)ethyl]-5-hydroxy-2-methylindole.

EXAMPLE 82

Reaction of the 3-[2-(2-cyclohexylmethylpiperidino)ethyl]-5-methoxy-2-methylindole described in Example 1 above with sodium hydride in DMF, and reaction of the resulting sodium salt with 2-pyridine carbonyl chloride using the procedure described above in Example 1 affords 1-(2-pyridylcarbonyl)-3-[2-(2-cyclohexylmethylpiperidino)ethyl]-5-methoxy-2-methylindole.

EXAMPLE 83

Reaction of 4-dimethylaminoaniline with benzoyl chloride in the presence of pyridine and reaction of the resulting N-(4-dimethylaminophenyl)benzamide with sodium hydride in DMF followed by reaction of the resulting sodium salt with chloramine all according to the procedure described above in Example 65 affords N'-benzoyl-4-dimethylaminophenylhydrazine. Reaction of the latter with 3-phthalimidopropyl methyl ketone in refluxing ethanol using the procedure described above in Example 1 affords 1-benzoyl-5-dimethylamino-2-methyl-3-(2-phthalimidoethyl)indole, which on refluxing in ethylene glycol dimethyl ether in the presence of a molar excess of hydrazine hydrate affords 1-benzoyl-3-(2-amimoethyl)-5-dimethylamino-2-methylindole. The latter, on reaction with one mole of isopropyl bromide in refluxing acetone in the presence of sodium carbonate affords 1-benzoyl-3-(2-isopropylaminoethyl)-5-dimethylamino-2-methylindole.

EXAMPLE 84

Reaction of 12.9 g. (0.035 mole) of 3-[2-(2-cyclohexylmethylpiperidino)ethyl]-5-methoxy-2-methylindole (described in Example 1) with 0.04 mole of a mineral oil dispersion of sodium hydride in 100 ml. of DMF; reaction of the resulting sodium salt with 6.8 g. (0.04 mole) of 4-chlorobenzoyl chloride; and isolation of the product in the form of the free base gave 6.3 g. of 1-(4-chlorobenzoyl)-3-[2-(2-cyclohexylmethylpiperidino)ethyl]-5-methoxy-2-methylindole, m.p. 69°–72° C. (from hexane).

EXAMPLE 85

Reaction of 7.01 g. (0.02 mole) of 3-[2-(N-benzyl-N-t-butylamino)ethyl]-5-methoxy-2-methylindole (described in Example 72) with 0.04 mole of a mineral oil dispersion of sodium hydride in 100 ml. of DMF; reaction of the resulting sodium salt with 6.34 g. (0.04 mole) of 4-fluorobenzoyl fluorobenzoyl chloride; and isolation of the product in the form of the hydrochloride salt gave 8.63 g. of 1-(4-fluorobenzoyl)-3-[2-(N-benzyl-N-t-butylamino)ethyl]-5-methoxy-2-methylindole hydrochloride, m.p. 137°–139° C. (from acetone/ether).

EXAMPLE 86

A solution of 9.6 g. (0.019 mole) of 1-(4-fluorobenzoyl)-3-[2-(N-benzyl-N-t-butylamino)ethyl]-5-methoxy-2-methylindole (described in Example 85) in 250 ml. of ethanol was reduced over 1 g. of 10% palladium-on-charcoal under a hydrogen pressure of about 40 pounds p.s.i.g. The product was worked up in the manner described above in Example 72 and isolated in the form of the hydrochloride salt to give 6.7 g. of 1-(4-fluorobenzoyl)-3-[2-(N-t-butylamino)ethyl]-5-methoxy-2-methylindole hydrochloride, m.p. 275°–276° C. (from ethanol).

EXAMPLE 87

Reaction of 11.54 g. (0.04 mole) of 3-[2-(diisopropylamino)ethyl]-5-methoxy-2-methylindole (described in Example 73) with 0.08 mole of a mineral oil dispersion of sodium hydride in 140 ml. of DMF; reaction of the resulting sodium salt with 12.7 g. (0.08 mole) of 4-fluorobenzoyl chloride; and isolation of the product in the form of the hydrochloride salt gave 11.62 g. of 1-(4-fluorobenzoyl)-3-[2-(diisopropylamino)ethyl]-5-methoxy-2-methylindole hydrochloride, m.p. 198°–199° C. (from acetone/ether).

EXAMPLE 88

A solution of 78.1 g. (0.84 mole) of 4-methylpyridine and 89.0 g. (0.84 mole) of benzaldehyde in 103 g. of acetic anhydride was heated with stirring under reflux for 24 hours. The mixture was then concentrated to a thick oil in vacuo and the residue dissolved in hot ethanol. The solid which separated was collected and recrystallized from ethanol to give 57.9 g. of 4-styrylpyridine, m.p. 131.5°–133° C.

The latter (36.2 g., 0.2 mole), dissolved in 220 ml. of absolute ethanol and 30 ml. of concentrated hydrochloric acid, was reduced over 3.0 g. of platinum oxide under a hydrogen pressure of about 55 pounds p.s.i.g. The product was worked up in the manner described above in Example 72 and isolated in the form of the hydrochloride salt to give 43.5 g. of 4-(2-cyclohexylethyl)piperidine hydrochloride, m.p. 246°–248° C.

A mixture of 72.4 g. (0.6 mole) 5-chloro-2-pentanone, 82.9 g. (0.6 mole) of anhydrous potassium carbonate and 58.6 g. (0.3 mole) of 4-(2-cyclohexylethyl)piperidine in 600 ml. of acetonitrile was refluxed with stirring for about 24 hours and worked up in the manner described above in Example 1. The product was isolated in the form of the hydrochloride salt to give 1-[4-(2-cyclohexylethyl)piperidino]pentan-4-one.

A solution of 9.4 g. (0.03 mole) of the latter and 5.5 g. (0.03 mole) of 4-methoxyphenylhydrazine hydrochloride in 80 ml. of absolute ethanol was heated under reflux for four and a half hours and then worked up in the manner described above in Example 1. The product was isolated in the form of the hydrochloride salt to give 6.3 g. of 3-{2-[4-(2-cyclohexylethyl)piperidino]ethyl}-5-methoxy-2-methylindole hydrochloride, m.p. 238°–240° C. (from ethanol/ether).

Reaction of 13.4 g. (0.035 mole) of the latter with 0.07 mole of a mineral oil dispersion of sodium hydride in 70 ml. of DMF; reaction of the resulting sodium salt with 11.1 g. (0.07 mole) of 4-fluorobenzoyl chloride and isolation of the product in the form of the hydrochloride salt gave 13.2 g. of 1-(4-fluorobenzoyl)-3-{2-[4-(2-cyclohexylethyl)piperidino]ethyl}-5-methoxy-2-methylindole hydrochloride, m.p. 241°–243° C. (from isopropanol/ether).

EXAMPLE 89

Reaction of 11.5 g. (0.03 mole) of 3-{2-[4-(2-cyclohexylethyl)piperidino]ethyl}-5-methoxy-2-methylindole (described in Example 88) with 0.045 mole of a mineral oil dispersion of sodium hydride in 150 ml. of DMF; reaction of the resulting sodium salt with 6.3 g. (0.045 mole) of benzoyl chloride; and isolation of the product in the form of the hydrochloride salt gave 12.8 g. of 1-benzoyl-3-{2-[4-(2-cyclohexylethyl)piperidino]ethyl}-5-methoxy-2-methylindole hydrochloride, m.p. 229°–230.5° C. (from ethanol/acetone).

EXAMPLE 90

4-Phenylpyridine (15.5 g., 0.1 mole) dissolved in 185 ml. of absolute ethanol and 15 ml. of concentrated hydrochloric acid was reduced with hydrogen over 2 g. of platinum oxide under a hydrogen pressure of about 55 pounds p.s.i.g. The product was worked up in the manner described above in Example 72 and isolated in the form of the hydrochloride salt to give 15.3 g. of 4-cyclohexylpiperidine hydrochloride. (The free base gives m.p. 106°–109° C.)

A mixture of 48.2 g. (0.4 mole) of 5-chloro-2-pentanone, 55.4 g. (0.4 mole) of anhydrous potassium carbonate and 21.1 g. 0.01 mole) of 4-cyclohexylpiperidine in 210 ml. of acetonitrile was refluxed with stirring for 74 hours and worked up in the manner described above in Example 1. The product was isolated in free base form to give 19.1 g. of 1-(4-cyclohexylpiperidino)pentan-4-one, b.p. 95°–101° C./0.04–0.05 mm., $n_D^{27}$ 1.4895. (Hydrochloride m.p. 204°–206° C.)

A solution of 3.49 g. (0.02 mole) of 4-methoxyphenylhydrazine hydrochloride and 5.76 g. (0.02 mole) of 1-(4-cyclohexylpiperidino)pentan-4-one hydrochloride in 50 ml. of absolute ethanol was heated under reflux for 7 hours and then worked up in the manner described above in Example 1. The product was isolated in the form of the hydrochloride salt to give 5.31 g. of 3-[2-(4-cyclohexylpiperidino)ethyl]-5-methoxy-2-methylindole hydrochloride, m.p. 231°–233° C. (from isopropanol/ether).

Reaction of 14.18 g. (0.04 mole) of the latter, in the form of the free base, with 3.36 g. (0.08 mole) of a mineral oil dispersion of sodium hydride in 125 ml. of DMF; reaction of the resulting sodium salt with 12.7 g. (0.08 mole) of 4-fluorobenzoyl chloride and isolation of the product in the form of the hydrochloride salt gave 9.6 g. of 1-(4-fluorobenozyl)-3-[2-(4-cyclohexylpiperidino)ethyl]-5-methoxy-2-methylindole hydrochloride, m.p. 241°–242.5° C. (from acetone).

EXAMPLE 91

To a mixture of 8.6 g. (0.36 mole) of magnesium turnings in 150 ml. of dry ether was added in small portions with cooling and stirring a solution of 45.0 g. (0.36 mole) of benzyl chloride in 75 ml. of anhydrous ether. When addition was complete, the mixture was stirred for about 1 hour and then treated dropwise with a solution of 26.6 g. of 4-chlorobutyronitrile in 95 ml. of ether. When addition was complete, the ether was gradually distilled off while replacing with an equal volume of toluene. The mixture was heated under reflux (at about 109° C.) for about 30 minutes, cooled to about 15° C., treated dropwise with 300 ml. of 10% aqueous ammonium chloride, filtered and the organic layer separated. The latter was washed with three 100 ml. portions of dilute hydrochloric acid, and the combined acid extracts were basified with solid potassium carbonate. Extraction of the mixture with ether and removal of the solvent from the combined organic extracts afforded an oil which was distilled in vacuo to give 13.05 g. of 2-benzoyl-4,5-dihydropyrrole, b.p. 123°–125° C./13 mm., $n_D^{25}$ 1.5405.

The latter, dissolved in 210 ml. of ethanol and 15 ml. of concentrated hydrochloric acid was reduced with hydrogen over 2 g. of platinum oxide under a hydrogen pressure of about 50 pounds p.s.i.g. The mixture was worked up in the manner described above in Example 72 and the product isolated in the form of the hydrochoride salt to give 16.8 g. of 2-cyclohexylmethylpyrrolidine hydrochloride, m.p. 130.5°–131.5° C. (from acetone).

A mixture of 18.4 g. (0.1 mole) of the latter in the form of the free base, 16.4 g. (0.1 mole) of 5-chloro-2-pentanone ethylene glycol ketal, 13.8 g. (0.1 mole) of anhydrous potassium carbonate and 16.6 g. (0.1 mole) of potassium iodide in 75 ml. of DMF was heated at 60°–70° C. for 5 hours and then worked up in the manner described above in Example 73. The product was isolated in the form of the free base to give 19.3 g. of 1-(2-cyclohexylmethylpyrrolidino)-4-pentanone ethylene glycol ketal, b.p. 122°–124° C./0.1 mm, $n_D^{25}$ 1.4838.

Reaction of 5.9 g. (0.02 mole) of the latter with 3.5 g. (0.02 mole) of 4-methoxyphenylhydrazine hydrochloride in a solution of 50 ml. of ethanol and 2.5 ml. of concentrated hydrochloric acid using the procedure described above in Example 1 and isolation of the product in the form of the free base gave 4.0 g. of 3-[2-(2-cyclohexylmethylpyrrolidino)ethyl]-5-methoxy-2-methylindole, m.p. 94.5°–96° C. (from hexane).

Reaction of the latter with a mineral oil dispersion of sodium hydride in DMF and reaction of the resulting sodium salt with 4-fluorobenzoyl chloride affords 1-(4-fluorobenzoyl)-3-[2-(2-cyclohexylmethylpyrrolidino)ethyl]-5-methoxy-2-methylindole.

EXAMPLE 92

Reaction of 3-[2-(2-cyclohexylmethylpyrrolidino)ethyl]-5-methoxy-2-methylindole with a mineral oil dispersion of sodium hydride in DMF and reaction of the resulting sodium salt with benzoyl chloride affords 1-benzoyl-3-[2-(2-cyclohexylmethylpyrrolidino)ethyl]-5-methoxy-2-methylindole.

EXAMPLE 93

To a suspension of 11.2 g. (1.6 mole) of lithium wire in 600 ml. of anhydrous ether was added dropwise 125.6 g. (0.8 mole) of bromobenzene. When addition was complete, the mixture was stirred for about a half hour and then treated dropwise first with a solution of 74.4 g. (0.8 mole) of picoline in 100 ml. of anhydrous ether and then with a solution of 74.0 g. (0.4 mole) of 2-phenylethyl bromide in 100 ml. of ether. The mixture was stirred at ambient temperature for about 12 hours and then poured with stirring onto 300 g. of ice. When all excess lithium had reacted, the layers were separated, the aqueous layer washed with additional ether and the combined organic portions dried and taken to dryness to give a residual oil which was distilled in vacuo to give 41.3 g. of 2-(3-phenylpropyl)pyridine, b.p. 76°–78° C./0.05 mm., $n_D^{25}$ 1.5592.

The latter (19.7 g., 0.1 mole) dissolved in 235 ml. of ethanol and 15 ml. of concentrated hydrochloric acid was reduced with hydrogen over 2 g. of platinum oxide under a hydrogen pressure of around 55 pounds p.s.i.g. at about 65° C. The product was worked up in the manner described above in Example 72 and isolated in the form of the hydrochloride salt to give 22.2 g. of 2-(3-cyclohexylpropyl)piperidine hydrochloride, m.p. 175°–176.5° C. (from ethyl acetate).

A mixture of 22.3 g. (0.1 mole) of the latter, 16.4 g. (0.1 mole) of 5-chloro-2-pentanone ethylene glycol ketal, 13.8 g. (0.1 mole) of anhydrous potassium carbonate and 16.6 g. (0.1 mole) of potassium iodide in 75 ml. of DMF was refluxed with stirring for 7 hours and worked up in the manner described above in Example 1. The product was isolated as the free base to give 26.4 g. of 1-[2-(3-cyclohexylpropyl)piperidino]pentan-4-one ethylene glycol ketal, b.p. 319°–144° C./0.08 mm., $n_D^{25}$ 1.4878.

A solution of 6.7 g. (0.02 mole) of the latter and 3.5 g. (0.02 mole) of 4-methoxyphenylhydrazine hydrochloride in 50 ml. of ethanol and 2.5 ml. of concentrated hydrochloric acid was refluxed for six hours and then worked up in the manner described above in Example 1. The product was isolated in the form of the free base to give 5.1 g. of 3-{2-[2-(3-cyclohexylpropyl)piperidino]ethyl}-5-methoxy-2-methylindole, m.p. 82°–83.5° C. (from hexane).

Reaction of the latter with a mineral oil dispersion of sodium hydride in DMF and reaction of the resulting sodium salt with 4-fluorobenzoyl chloride affords 1-(4-fluorobenzoyl)-3-{2-[2-(3-cyclohexylpropyl)piperidino]ethyl}-5-methoxy-2-methylindole.

EXAMPLE 94

Reaction of 3-{2-[2-(3-cyclohexylpropyl)piperidino]ethyl}-5-methoxy-2-methylindole with a mineral oil dispersion of sodium hydride in DMF and reaction of the resulting sodium salt with 4-fluorobenzoyl chloride affords 1-benzoyl-3-{2-[2-(3-cyclohexylpropyl)piperidino]ethyl}-5-methoxy-2-methylindole.

EXAMPLE 95

Reduction of 3-benzylpyridine with hydrogen over a platinum oxide catalyst in an acid medium affords 3-cyclohexylmethylpiperidine which, on reaction with 5-chloro-2-pentanone in acetonitrile in the presence of sodium carbonate affords 1-(3-cyclohexylmethylpiperidino)pentan-4-one.

Reaction of the latter with 4-nitrophenylhydrazine in refluxing ethanol affords 3-[2-(3-cyclohexylmethylpiperidino)-ethyl]-5-nitro-2-methylindole.

Reaction of the latter with a mineral oil dispersion of sodium hydride in DMF and reaction of the resulting sodium salt with benzoyl chloride affords 1-benzoyl-3-[2-(3-cyclohexylmethylpiperidino)ethyl]-5-nitro-2-methylindole which, on reduction with hydrogen over palladium-on-charcoal affords 1-benzoyl-3-[2-(3-cyclohexylmethylpiperidino)ethyl]-5-amino-2-methylindole.

EXAMPLE 96

Reaction of the 1-benzoyl-3-[2-(3-cyclohexylmethylpiperidino)ethyl]-5-amino-2-methylindole described above in Example 95 with formaldehyde and formic acid affords 1-benzoyl-3-[2-(3-cyclohexylmethylpiperidino)ethyl]-5-methylamino-2-methylindole.

EXAMPLE 97

Reaction of 1-methylpiperazine with 5-chloro-2-pentanone in acetonitrile in the presence of sodium carbonate affords 1-(4-methyl-1-piperazino)pentan-4-one.

Reaction of the latter with 4-methoxyphenylhydrazine in refluxing ethanol affords 3-[2-(4-methyl-1-piperazino)ethyl]-5-methoxy-2-methylindole.

Reaction of the latter with a mineral oil dispersion of sodium hydride in DMF and reaction of the resulting sodium salt with benzoyl chloride affords 1-benzoyl-3-[2-(4-methyl-1-piperazino)ethyl]-5-methoxy-2-methylindole.

EXAMPLE 98

Reduction of 3-methylpyridine with hydrogen over platinum oxide in an acid medium affords 3-methylpiperidine which on reaction with 5-chloro-2-pentanone in acetonitrile in the presence of sodium carbonate affords 1-(3-methylpiperidino)pentan-4-one.

Reaction of the latter with 4-methoxyphenylhydrazine in refluxing ethanol affords 3-[2-(3-methylpiperidino)ethyl]-5-methoxy-2-methylindole.

Reaction of the latter with a mineral oil dispersion of sodium hydride in DMF and reaction of the resulting sodium salt with benzoyl chloride affords 1-benzoyl-3-[2-(3-methylpiperidino)ethyl]-5-methoxy-2-methylindole.

The compounds of the invention have been tested in the carrageenin edema (CE) and adjuvant arthritis (AA) tests and found to have anti-inflammatory activity. Data so-obtained, stated in terms of percent inhibition at a dose expressed in terms of millimoles (μM)/kg., are given below. All data were obtained on oral administration.

| Example | CE (% Inhib./μM/kg.) | AA (% Inhib./μM/kg.) |
|---|---|---|
| 1 | 44%/0.324 | 79%/0.1 |
| 2 | 38%/0.324 | 37%/0.08 |
| 3 | 45%/0.324 | 64%/0.18 |
| 4 | 47%/0.324 | 28%/0.02 |
|  |  | 80%/0.324 |
| 5 | 26%/0.324 | 0%/0.08 |
| 6 | 65%/0.08 | 66%/0.02 |
|  |  | 84%/0.08 |
| 7 | 30%/0.324 | 29%/0.08 |
| 8 | 37%/0.324 | 30%/0.08 |
| 9 | — | 72%/0.162 |
| 10 | — | 63%/0.324 |
| 11 | 43%/0.324 | 50%/0.324 |
| 12 | 17%/0.08 | 17%/0.08 |
|  | 17%/0.324 |  |
| 48 | 28%/0.08 | 33%/0.08 |
|  | 38%/0.324 |  |
| 50 | 59%/0.324 | 87%/0.162 |
| 58 | 56%/0.324 | 51%/0.08 |
| 62 | 57%/0.324 | 107%/0.324 |
| 63 | 59%/0.08 | 84%/0.08 |
|  | 79%/0.324 |  |
| 64 | 16%/0.02 | 36%/0.01 |
|  | 37%/0.08 | 70%/0.04 |
|  | 57%/0.324 | 100%/0.16 |
| 65 | 32%, 42%/0.02 | 85%/0.08 |
|  | 63%, 65%/0.08 |  |
| 67 | 0%/0.02 | 25%/0.08 |
|  | 15%/0.08 |  |
| 72 (N-Benzyl) | 11%/0.02 | 62%/0.08 |
| 72 (N—H) | 27%/0.08 | Toxic/0.16 |
|  | 19%/0.08 |  |
|  | 56%/0.324 |  |
| 73 | 39%/0.08 | 0%/0.005 |
|  | 61%/0.324 | 0%/0.02 |
|  |  | 53%/0.08 |
| 84 | 16%/0.02 | 36%/0.01 |
|  | 37%/0.08 | 70%/0.04 |
|  | 57%/0.32 | 100%/0.16 |
| 85 | 40%/0.08 | 0%/0.005 |
|  | 56%/0.324 | 11%/0.02 |
|  |  | 104%/0.08 |
| 86 | 49%/0.08 | 13%/0.005 |
|  | 54%/0.324 | 71%/0.02 |
|  |  | Toxic/0.08 |
| 87 | 47%/0.08 | 43%/0.005 |
|  | 61%/0.324 | 73%/0.02 |
|  |  | 98%/0.08 |
| 88 | 0%/0.02 | 75%/0.08 |
|  | 26%/0.08 |  |
| 89 | 16%/0.02 | 89%/0.08 |
|  | 32%/0.08 |  |
| 90 | 13%/0.08 | 77%/0.08 |
|  | 22%/0.324 |  |

I claim:
1. A compound having the formula

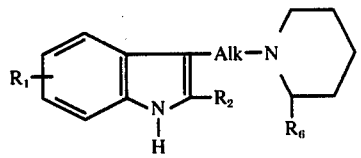

where $R_1$ is trifluoromethoxy; $R_2$ is lower-alkyl, $R_6$ is cycloalkyl-lower-alkyl, and Alk is lower-alkylene.

2. 3-[2-(2-Cyclohexylmethylpiperidino)ethyl]-5-trifluoromethoxy-2-methylindole according to claim 1.

* * * * *

UNITED STATES PATENT AND TRADEMARK OFFICE
CERTIFICATE OF CORRECTION

PATENT NO. : 4,021,431       Page 1 of 2

DATED : May 3, 1977

INVENTOR(S) : Bernard L. Zenitz

It is certified that error appears in the above-identified patent and that said Letters Patent are hereby corrected as shown below:

Column 1, line 65, before "term" insert --the--.

Colum 1, line 66, change "derivved" to read --derived--.

Column 2, line 26, change "strond" to read --strong--.

Column 2, line 29, change "lower-alkoide to read --lower-alkoxide--.

Column 2, line 30, change "exmple" to read --example--.

Column 2, line 60, change "material" to read --materials--.

Column 4, line 11, change "catlytic" to read --catalytic--.

Column 4, line 57, before "$R_8$" insert --and--.

UNITED STATES PATENT AND TRADEMARK OFFICE
CERTIFICATE OF CORRECTION

PATENT NO. : 4,021,431

DATED : May 3, 1977

INVENTOR(S) : Bernard L. Zenitz

It is certified that error appears in the above—identified patent and that said Letters Patent is hereby corrected as shown below:

Column 5, line 44, before "$R_6$" insert --and--.

Column 6, line 23, change "temperture" to read --temperature--.

Column 6, line 63, change "enert" to read --inert--.

Column 7, line 11, change "off" to read --of--.

Column 12, line 38, change "methanesulfonic aicd" to read --methanesulfonic acid--.

Column 13, line 25, change "if" to read --is--.

Column 13, line 39, change "are" to read --were--.

Column 13, line 58, after "5.0" insert -- ml.--.

Signed and Sealed this

Fifteenth Day of June 1982

[SEAL]

Attest:

GERALD J. MOSSINGHOFF

Attesting Officer   Commissioner of Patents and Trademarks